(12) United States Patent
Li et al.

(10) Patent No.: US 10,327,472 B2
(45) Date of Patent: Jun. 25, 2019

(54) PRE-VAPORIZATION FORMULATION FOR CONTROLLING ACIDITY IN AN E-VAPING DEVICE

(71) Applicant: Altria Client Services LLC, Richmond, VA (US)

(72) Inventors: San Li, Midlothian, VA (US); Georgios Karles, Richmond, VA (US); Gerd Kobal, Sandy Hook, VA (US); Weiling Li, Moseley, VA (US); Rebecca Secrist, Petersburg, VA (US); Maria Del Carmen Jarquin, Henrico, VA (US); Christopher Di Novi, Richmond, VA (US); Yezdi Pithawalla, Richmond, VA (US); David Kane, Richmond, VA (US)

(73) Assignee: Altria Client Services LLC, Richmond, VA (US)

( * ) Notice: Subject to any disclaimer, the term of this patent is extended or adjusted under 35 U.S.C. 154(b) by 759 days.

(21) Appl. No.: 14/865,813

(22) Filed: Sep. 25, 2015

(65) Prior Publication Data

US 2017/0086500 A1 Mar. 30, 2017

(51) Int. Cl.
*A24F 47/00* (2006.01)
*A24B 15/16* (2006.01)
(Continued)

(52) U.S. Cl.
CPC ............ *A24F 47/008* (2013.01); *A24B 15/16* (2013.01); *A24B 15/167* (2016.11); *A24B 15/30* (2013.01); *A24B 15/42* (2013.01); *A61K 9/007* (2013.01)

(58) Field of Classification Search
None
See application file for complete search history.

(56) References Cited

U.S. PATENT DOCUMENTS

2006/0174901 A1   8/2006   Karles et al.
2012/0006342 A1   1/2012   Rose et al.
(Continued)

FOREIGN PATENT DOCUMENTS

WO   WO-0238208 A2    5/2002
WO   WO-2006004646 A1  1/2006
(Continued)

OTHER PUBLICATIONS

Burch, S.G. et al., "Effect of pH on Nicotine Absorption and Side Effects Produced by Aerosolized Nicotine," Journal of Aerosol Medicine, vol. 6, No. 1, 1993, pp. 45-52.
(Continued)

*Primary Examiner* — Michael J Felton
*Assistant Examiner* — Katherine A Will
(74) *Attorney, Agent, or Firm* — Harness, Dickey & Pierce, P.L.C.

(57) ABSTRACT

A pre-vaporization formulation for an e-vaping device includes a vapor former, optionally water, nicotine, nicotine bitartrate and an acid. The pH of the pre-vaporization formulation is between about 4 and about 6. The acid can include one or more of pyruvic acid, formic acid, oxalic acid, glycolic acid, acetic acid, isovaleric acid, valeric acid, propionic acid, octanoic acid, lactic acid, sorbic acid, malic acid, tartaric acid, succinic acid, citric acid, benzoic acid, oleic acid, aconitic acid, butyric acid, cinnamic acid, decanoic acid, 3,7-diemthyl-6-octenoic acid, 1-glutamic acid, heptanoic acid, hexanoic acid, 3-hexenoic acid, trans-2-hexenoic acid, isobutyric acid, lauric acid, 2-methylbutyric acid, 2-methylvaleric acid, myristic acid, nonanoic acid, palmitic acid, 4-pentenoic acid, phenylacetic acid, 3-phenylpropionic acid, hydrochloric acid, phosphoric acid and sulfuric acid.

23 Claims, 3 Drawing Sheets

(51) Int. Cl.
*A24B 15/30* (2006.01)
*A24B 15/42* (2006.01)
*A61K 9/00* (2006.01)

(56) References Cited

U.S. PATENT DOCUMENTS

| | | |
|---|---|---|
| 2013/0192615 A1 | 8/2013 | Tucker et al. |
| 2013/0192620 A1 | 8/2013 | Tucker et al. |
| 2013/0228191 A1* | 9/2013 | Newton ................ A24F 47/008 131/329 |
| 2014/0271946 A1 | 9/2014 | Kobal et al. |
| 2014/0345631 A1 | 11/2014 | Bowen et al. |
| 2014/0345635 A1 | 11/2014 | Rabinowitz et al. |
| 2015/0020823 A1 | 1/2015 | Lipowicz et al. |
| 2015/0027454 A1 | 1/2015 | Li et al. |
| 2015/0027468 A1 | 1/2015 | Li et al. |
| 2018/0043113 A1* | 2/2018 | Hogwood ............. A61M 15/06 |

FOREIGN PATENT DOCUMENTS

| | | |
|---|---|---|
| WO | WO-2007078273 A1 | 7/2007 |
| WO | WO-2012134380 A1 | 10/2012 |
| WO | WO-2014182736 A1 | 11/2014 |
| WO | WO-2015084544 A1 | 6/2015 |
| WO | WO-2015167629 A1 | 11/2015 |

OTHER PUBLICATIONS

International Search Report and Written Opinion dated Dec. 22, 2016 for corresponding application No. PCT/EP2016/072772.

* cited by examiner

FIG. 3

PRE-VAPORIZATION FORMULATION FOR CONTROLLING ACIDITY IN AN E-VAPING DEVICE

BACKGROUND

Field

Example embodiments relate generally to a pre-vaporization formulation for e-vaping devices configured to control the acidity in the e-vaping device.

Related Art

Electronic vaping devices (or e-vaping devices) are used to vaporize a pre-vaporization formulation such as, for example, a liquid material, into a vapor to be inhaled by an adult vaper. E-vaping devices typically include a heater that is configured to vaporize the pre-vaporization formulation to produce the vapor. An e-vaping device may include several e-vaping elements including a power source, a cartridge or e-vaping tank including the heater, and a reservoir holding the pre-vaporization formulation. For example, the pre-vaporization formulation may include a liquid, solid and/or gel formulation including, but not limited to, water, beads, solvents, active ingredients, ethanol, plant extracts, natural or artificial flavors, and/or vapor formers such as glycerine and/or propylene glycol.

Typically, a tobacco-based smoking article produces a vapor known to create a desired sensory experience for an adult smoker, including a low to moderate harshness response in the throat and a perceived warmth or strength in the chest of the adult smoker. With respect to e-vaping devices, the harshness of the vapor, which is typically understood as the sensation experienced in the throat of an adult vaper, and the strength of the vapor, which is typically understood as the sensation experienced in the chest of the adult vaper, may vary based on the contents and concentrations of the pre-vaporization formulation used to form the vapor inhaled by the adult vaper, including but not limited to the concentration of nicotine in the vapor. In some cases, for a similar amount of nicotine, an e-vaping device delivers substantially more nicotine in the gas phase to the adult vaper than a tobacco-based product delivers in the gas phase, which increases the harshness of the vapor, and degrades the sensory experience of the adult vaper as a result of the increased harshness. Accordingly, acids can be added to the pre-vaporization formulation to reduce the amount of nicotine present in the gas phase generated by the e-vaping device. However, a level of acid in the pre-vaporization formulation that is too high may also degrade the taste of the vapor.

SUMMARY OF THE INVENTION

The pre-vaporization formulation of an e-vaping device is configured to form a vapor having a particulate phase and a gas phase when heated by the heater in the e-vaping device. At least one example embodiment relates to an e-vaping device configured to provide a greater proportion of nicotine in the particulate phase than in the gas phase without increasing the acidity of the vapor generated by the e-vaping device.

At least one example embodiment relates to an e-vaping device that is configured to provide a perceived sensory experience for adult vapers that is similar to the sensory experience enjoyed while smoking a tobacco-based product.

Another example embodiment relates to an e-vaping device that is configured to provide a sensory experience including levels of harshness in the throat and perceived strength or warmth in the chest that are similar to those experienced when smoking a tobacco-based product. In achieving a desirable balance of strength and harshness, the strength of the e-vaping product may be increased without increasing the harshness thereof.

In at least one embodiment, a pre-vaporization formulation of an e-vaping device includes a mixture of a vapor former, optionally water, nicotine and one or more acids. The acids may be operative upon the vapor generated by the e-vaping device so as to reduce an amount of nicotine content in the gas phase of the vapor. For example, the one or more acids have a boiling point of at least about 100° C. and are configured to volatilize when heated by a heater in the e-vaping device. Various acids may have different strengths and thus have different degrees of influence on the reduction of nicotine in the vapor.

In at least one embodiment, in the pre-vaporization formulation, a dynamic equilibrium typically exists between dissociated and non-dissociated acid molecules, protonated and non-protonated nicotine molecules with each species concentration depending on the strength of the acid (or acids) and the respective concentrations of acid (or acids) and nicotine in the formulation. Protonated nicotine (tied by the conjugated acid base as in a salt) is less volatile than non-protonated nicotine. Hence, as the acid concentration increases (or the acid strength at the same acid concentration increases) more protonated nicotine is formed. When the pre-vaporization formulation is heated, the components of the formulation are vaporized, and upon subsequent cooling, the components of the formulation condense to form a vapor. The increased presence of nicotine in protonated form or forms, due to the inclusion of acid or acids, binds the nicotine in the aerosol particles and reduces its availability to the gas phase of the vapor. As a result of the lower content of nicotine in the gas phase, the amount of perceived throat harshness by an adult vaper is reduced. Accordingly, the acid combination included in the pre-vaporization formulation reduces gas phase nicotine when the pre-vaporization formulation is heated by forming a nicotine salt, and thereby reduces transfer efficiency of the nicotine from the particulate phase to the gas phase. As a result of the lower content of nicotine in the gas phase, the amount of perceived throat harshness by an adult vaper is reduced.

In at least one embodiment, the pre-vaporization formulation includes a mixture of a vapor former and water in a ratio of about 80/20, nicotine in an amount of up to 3% by weight, about 1% nicotine bitartrate salt, about 0.5% pyruvic acid and about 0.25% acetic acid. The resulting vapor has a lowered harshness compared to a similar formulation that does not include the acids.

In at least one embodiment, the one or more acids have a liquid to vapor transfer efficiency of about 50% or greater, and are included in the pre-vaporization formulation in an amount sufficient to reduce the nicotine gas phase component by about 70% by weight or greater. In other embodiments, the one or more acids are included in an amount that is sufficient to reduce the nicotine gas phase component by about 40% to about 70% by weight.

In at least one embodiment, a method of reducing perceived throat harshness of a vaporized formulation of an e-vaping device including nicotine includes adding one or more acids to the pre-vaporization formulation in an amount sufficient to reduce the perceived throat harshness without degrading the taste of the vapor.

In at least one embodiment, a concentration of nicotine in the gas phase is equal to or smaller than substantially 1% by weight of the total nicotine delivered. As a result, substantially 99% of the total nicotine delivered in the vapor is in the particulate phase.

In at least one embodiment, the combination of acids includes a combination of pyruvic acid, formic acid, oxalic acid, glycolic acid, acetic acid, isovaleric acid, valeric acid, propionic acid, octanoic acid, lactic acid, sorbic acid, malic acid, tartaric acid, succinic acid, citric acid, benzoic acid, oleic acid, aconitic acid, butyric acid, cinnamic acid, decanoic acid, 3,7-dimethyl-6-octenoic acid, 1-glutamic acid, heptanoic acid, hexanoic acid, 3-hexenoic acid, trans-2-hexenoic acid, isobutyric acid, lauric acid, 2-methylbutyric acid, 2-methylvaleric acid, myristic acid, nonanoic acid, palmitic acid, 4-pentenoic acid, phenylacetic acid, 3-phenylpropionic acid, hydrochloric acid, phosphoric acid and sulfuric acid.

In at least one embodiment, the combination of acids includes pyruvic acid, tartaric acid and acetic acid.

In at least one embodiment, the concentration of the combination of acids is between substantially 0.25% by weight and substantially 2% by weight. The concentration of the combination of acids may also be between substantially 0.5% by weight and substantially 1.5% by weight, or between substantially 1.5% by weight and substantially 2% by weight. The combination of acids may include between 2 and 10 acids. For example, the combination of acids may include 3 acids. The combination of acids may also include substantially equal parts of each individual acid included in the combination. For example, the combination of acids may include substantially equal parts of pyruvic acid, tartaric acid and acetic acid. Alternatively, the combination of acids may include more of the pyruvic acid than one or more of the tartaric acid and the acetic acid.

In at least one embodiment, the concentration of the nicotine in the pre-vaporization formulation is between substantially 1.5% by weight and substantially 6% by weight. The concentration of the nicotine in the pre-vaporization formulation may also be between substantially 3% by weight and substantially 5% by weight. However, in example embodiments, the concentration of the nicotine in the gas phase of the vapor is less than about 1.5%. In example embodiments, the concentration of the nicotine in the gas phase of the vapor is about 2% or less, about 1%, about 0.5% or about 0.1%.

In at least one embodiment, the pre-vaporization formulation includes substantially 3% nicotine by weight, substantially 0.5% pyruvic acid, substantially 0.4% tartaric acid and 0.1% substantially acetic acid.

In at least one embodiment, the pre-vaporization formulation includes substantially 3% nicotine by weight, substantially 0.5% to 1% nicotine bitartrate, substantially 0.5% pyruvic acid, substantially 0.4% lactic acid and substantially 0.1% hydrochloric acid.

In at least one embodiment, the pre-vaporization formulation includes substantially 3% nicotine by weight, substantially 0.5% nicotine bitartrate and substantially 0.2% hydrochloric acid.

In at least one embodiment, the pre-vaporization formulation includes substantially 3% nicotine by weight, substantially 0.5% to 1% nicotine bitartrate, substantially 0.5% pyruvic acid, substantially 0.4% lactic acid and substantially 0.5% tartaric acid.

In at least one embodiment, the pre-vaporization formulation includes substantially 3% nicotine by weight, substantially 0.5% to 1% nicotine bitartrate, substantially 0.5% pyruvic acid, substantially 0.4% lactic acid, substantially 0.1% benzoic acid and substantially 0.1% oleic acid.

In at least one embodiment, the pre-vaporization formulation includes substantially 3% nicotine by weight, substantially 1% nicotine bitartrate, substantially 0.5% pyruvic acid, substantially 0.2% acetic acid and substantially 0.1% tartaric acid.

In at least one embodiment, the pre-vaporization formulation includes substantially 3% nicotine by weight, substantially 0.5% nicotine bitartrate, substantially 0.5% pyruvic acid, substantially 0.4% lactic acid, substantially 0.1% benzoic acid and substantially 1% oleic acid.

In at least one embodiment, the pre-vaporization formulation includes substantially 3% to 5% nicotine by weight, substantially 1% to 2% nicotine bitartrate and substantially 0.4% to 0.9% acetic acid. For example, the pre-vaporization formulation includes substantially 3% nicotine by weight, substantially 1% nicotine bitartrate and substantially 0.4% acetic acid.

In at least one embodiment, the pre-vaporization formulation includes substantially 3% to 5% nicotine by weight, substantially 0.5% to 1% nicotine bitartrate and substantially 0.5% to 1% of a mixture of substantially equal parts pyruvic acid, benzoic acid, lactic acid and acetic acid.

In at least one embodiment, the pre-vaporization formulation includes substantially 3% to 5% nicotine by weight, substantially 0.5% to 1% nicotine bitartrate and substantially 0.01% to 0.1% hydrochloric acid.

In at least one embodiment, the pre-vaporization formulation includes substantially 3% to 5% nicotine by weight, substantially 0.5% to 1% nicotine bitartrate, substantially 0.5% to 1% oleic acid and substantially 0.5% to 1.5% of a mixture of substantially equal parts pyruvic acid, tartaric acid and acetic acid.

In at least one embodiment, the pre-vaporization formulation includes substantially 3% to 5% nicotine by weight, substantially 0.5% nicotine bitartrate, substantially 0.1% to 0.5% sorbic acid, substantially 0.1% to 0.5% tartaric acid and substantially 0.1% to 0.75% pyruvic acid. For example, when the concentration of nicotine by weight is substantially 5%, hydrochloric acid may be added at a concentration of substantially 0.01% to 0.1%.

In at least one embodiment, the pre-vaporization formulation includes substantially 3% to 5% nicotine by weight, substantially 0.5% nicotine bitartrate, substantially 0.1% to 0.5% succinic acid, substantially 0.1% to 0.75% pyruvic acid and substantially 0.1% to 0.5% lactic acid. For example, when the concentration of nicotine by weight is substantially 5%, hydrochloric acid may be added at a concentration of substantially 0.01% to 0.1%, or tartaric acid may be added at a concentration of substantially 0.1% to 0.25%.

In at least one embodiment, a pre-vaporization formulation includes a combination of pyruvic acid, tartaric acid and acetic acid. The pyruvic acid, tartaric acid and acetic acid may be in equal proportions. In addition, the resulting vapor generated by the pre-vaporization formulation may include an amount of nicotine in the gas phase of less than or equal to substantially 1% of the total nicotine delivered. As a result, about 99% of the total nicotine delivered in the vapor is in the particulate phase. The above combination of the pyruvic acid, tartaric acid and acetic acid, together with the nicotine concentration in the gas phase of the vapor of equal to or less than substantially 1% of the total nicotine delivered, results in an inhalable vapor that has a combination of warmth in chest and higher concentrations of nicotine in the gas phase without an increase in harshness and resulting degradation of the taste experienced by the adult vaper.

In various example embodiments, the pre-vaporization formulation results in the reduction and the maintenance of vapor pH, improves sensory experience with respect to harshness, reduces nicotine and acid evaporation, and improves the performance of the e-vaping device by reducing undesired deposits that typically form inside the e-vaping device, without increasing the acidity of the resulting vapor to a level that would degrade the taste of the vapor.

BRIEF DESCRIPTION OF THE DRAWINGS

The above and other features and advantages of example embodiments will become more apparent by describing in detail, example embodiments with reference to the attached drawings. The accompanying drawings are intended to depict example embodiments and should not be interpreted to limit the intended scope of the claims. The accompanying drawings are not to be considered as drawn to scale unless explicitly noted.

DETAILED DESCRIPTION

Some detailed example embodiments are disclosed herein. However, specific structural and functional details disclosed herein are merely representative for purposes of describing example embodiments. Example embodiments may, however, be embodied in many alternate forms and should not be construed as limited to only the embodiments set forth herein.

Accordingly, while example embodiments are capable of various modifications and alternative forms, embodiments thereof are shown by way of example in the drawings and will herein be described in detail. It should be understood, however, that there is no intent to limit example embodiments to the particular forms disclosed, but to the contrary, example embodiments are to cover all modifications, equivalents, and alternatives falling within the scope of example embodiments. Like numbers refer to like elements throughout the description of the figures.

It should be understood that when an element or layer is referred to as being "on," "connected to," "coupled to," or "covering" another element or layer, it may be directly on, connected to, coupled to, or covering the other element or layer or intervening elements or layers may be present. In contrast, when an element is referred to as being "directly on," "directly connected to," or "directly coupled to" another element or layer, there are no intervening elements or layers present. Like numbers refer to like elements throughout the specification. As used herein, the term "and/or" includes any and all combinations of one or more of the associated listed items.

It should be understood that, although the terms first, second, third, etc. may be used herein to describe various elements, components, regions, layers and/or sections, these elements, components, regions, layers, and/or sections should not be limited by these terms. These terms are only used to distinguish one element, component, region, layer, or section from another region, layer, or section. Thus, a first element, component, region, layer, or section discussed below could be termed a second element, component, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing. Thus, the regions illustrated in the figures are schematic in nature and their shapes are not intended to illustrate the actual shape of a region of a device and are not intended to limit the scope of example embodiments.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

When the terms "about" or "substantially" are used in this specification in connection with a numerical value, it is intended that the associated numerical value include a tolerance of ±10% around the stated numerical value. Moreover, when reference is made to percentages in this specification, it is intended that those percentages are based on weight, i.e., weight percentages. The expression "up to" includes amounts of zero to the expressed upper limit and all values therebetween. When ranges are specified, the range includes all values therebetween such as increments of 0.1%.

Moreover, when the words "generally" and "substantially" are used in connection with geometric shapes, it is intended that precision of the geometric shape is not required but that latitude for the shape is within the scope of the disclosure. Although the tubular elements of the embodiments may be cylindrical, other tubular cross-sectional forms are contemplated, such as square, rectangular, oval, triangular and others.

As used herein, the term "vapor former" describes any suitable known compound or mixture of compounds that, in use, facilitates formation of a vapor and that is substantially resistant to thermal degradation at the operating temperature of the vapor-generating device. Suitable vapor-formers consist of various compositions of polyhydric alcohols such as propylene glycol. In at least one embodiment, the vapor former is propylene glycol.

Figure 1:
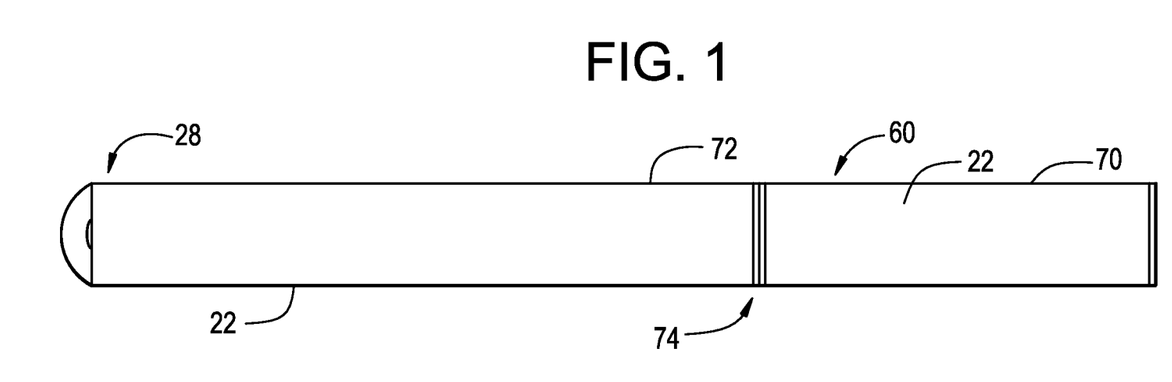
FIG. 1 is a side view of an e-vaping device, according to an example embodiment.

FIG. 1 is a side view of an e-vaping device 60, according to an example embodiment. In FIG. 1, the e-vaping device 60 includes a first section or cartomizer 70 and a second section 72, which are coupled together at a threaded joint 74 or by other connecting structure such as a snug-fit, snap-fit, detent, clamp and/or clasp or the like. In one embodiment, the first section or cartomizer 70 may be a replaceable cartridge and the second section 72 may be a reusable section. Alternatively, the first section or cartomizer 70 and the second section 72 may be integrally formed in one piece.

Figure 2:
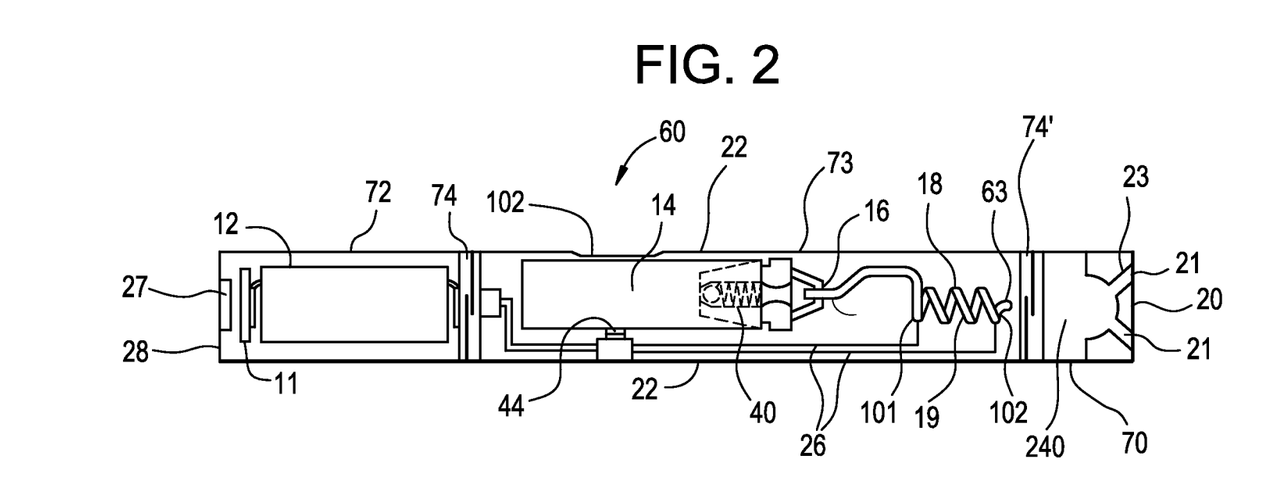
FIG. 2 is a longitudinal cross-sectional view of an e-vaping device, according to an example embodiment.

FIG. 2 is a cross-sectional view of an example embodiment of an e-vaping device. As shown in FIG. 2, the first section or cartomizer 70 can house a mouth-end insert 20, a capillary vapor generator including a capillary tube 18, a heater 19 to heat at least a portion of the capillary tube 18, and a reservoir 14.

The second section 72 can house a power supply 12, a control circuitry 11 configured to control the power supply 12, and a puff sensor 16. The puff sensor is configured to sense when an adult vaper is puffing on the e-vaping device 60, which triggers operation of the power supply 12 via the control circuitry 11 to activate the heater 19 to heat the pre-vaporization formulation housed in the reservoir 14 and form a vapor. A threaded portion 74 of the second section 72 can be connected to a battery charger, when not connected to the first section or cartomizer 70, to charge the battery or power supply 12.

As shown in FIG. 2, in other example embodiments, a valve 40 can be a two-way valve, and the reservoir 14 can be pressurized. For example, the reservoir 14 can be pressurized using a pressurization arrangement 405 configured to apply constant pressure to the reservoir 14. As such, emission of vapor formed via heating of the pre-vaporization formulation housed in the reservoir 14 is facilitated.

In example embodiments, the capillary tube 18 is formed of or includes a conductive material, and thus acts as its own heater 19 by passing current through the tube. The capillary tube 18 may be any electrically conductive material capable of being resistively heated, while retaining the necessary structural integrity at the operating temperatures experienced by the capillary tube 18, and which is non-reactive with the pre-vaporization formulation. Suitable materials for forming the capillary tube 18 are one or more of stainless steel, copper, copper alloys, porous ceramic materials coated with film resistive material, nickel-chromium alloys, and combinations thereof. For example, the capillary tube 18 is a stainless steel capillary tube 18 and serves as a heater 19 via electrical leads 26 attached thereto for passage of direct or alternating current along a length of the capillary tube 18. Thus, the stainless steel capillary tube 18 is heated by resistance heating. Alternatively, the capillary tube 18 may be a non-metallic tube such as, for example, a glass tube. In such an embodiment, the heater 19 is formed of or includes a conductive material capable of being resistively heated, such as, for example, stainless steel, nichrome or platinum wire, arranged along the glass tube. When the heater arranged along the glass tube is heated, pre-vaporization formulation in the capillary tube 18 is heated to a temperature sufficient to at least partially volatilize pre-vaporization formulation in the capillary tube 18.

In at least one embodiment, at least two electrical leads 26 are bonded to the metallic capillary tube 18. In at least one embodiment, one electrical lead 26 is coupled to a first, upstream portion 101 of the capillary tube 18 and a second electrical lead 26 is coupled to a downstream, end portion 102 of the capillary tube 18.

In operation, when an adult vaper puffs on the e-vaping device, the puff sensor 16 detects a pressure gradient caused by the puffing of the adult vaper, and the control circuitry 11 activates the heater 19 to heat the pre-vaporization formulation located in the reservoir 14. Once the capillary tube 18 is heated, the pre-vaporization formulation contained within a heated portion of the capillary tube 18 is volatilized and expressed out of the outlet 63, where the pre-vaporization formulation expands and mixes with air and forms a vapor in mixing chamber 240.

The power supply 12 of example embodiments can include a battery arranged in the second section 72 of the e-vaping device 60. The power supply 12 is configured to apply voltage across the heater 19, and the heater 19 volatilizes the pre-vaporization formulation housed in the reservoir 14.

In at least one embodiment, the electrical contacts or connection between the heater 19 and the electrical leads 26 are substantially conductive and temperature resistant while the heater 19 is substantially resistive so that heat generation occurs primarily along the heater 19 and not at the contacts.

The power supply or battery 12 may be rechargeable and include circuitry allowing the battery to be chargeable by an external charging device. In this case, the circuitry, when charged, provides power for a pre-determined number of puffs, after which the circuitry may have to be re-connected to an external charging device.

In at least one embodiment, the e-vaping device 60 may include control circuitry which can be on a printed circuit board 11. The control circuitry 11 may also include a heater activation light 27 that is configured to glow when the heater 19 is activated. In at least one embodiment, the heater activation light 27 comprises at least one LED and is at a distal end 28 of the e-vaping device 60 so that the heater activation light 27 illuminates a cap which takes on the appearance of a burning coal during a puff. Moreover, the heater activation light 27 can be configured to be visible to the adult vaper. The light 27 may also be configured such that the adult vaper can activate and/or deactivate the light 27 when desired, such that the light 27 would not activate during vaping if desired.

In at least one embodiment, the e-vaping device 60 further includes a mouth-end insert 20 having at least two off-axis, diverging outlets 21. In at least one embodiment, the mouth-end insert 20 includes at least two diverging outlets 21 (e.g., 3 to 8 outlets or more). In at least one embodiment, the outlets 21 of the mouth-end insert 20 are located at ends of off-axis passages 23 and are angled outwardly in relation to the longitudinal direction of the e-vaping device 60 (i.e., divergently). As used herein, the term "off-axis" denotes an angle to the longitudinal direction of the e-vaping device. Also, the mouth-end insert (or flow guide) 20 may include outlets uniformly distributed around the mouth-end insert 20 so as to substantially uniformly distribute vapor in an adult vaper's mouth during use.

In at least one embodiment, the e-vaping device 60 is about the same size as a conventional tobacco-based product. In some embodiments, the e-vaping device 60 may be about 80 mm to about 110 mm long, for example about 80 mm to about 100 mm long and about 7 mm to about 10 mm in diameter.

The outer cylindrical housing 22 of the e-vaping device 60 may be formed of or include any suitable material or combination of materials. In at least one embodiment, the outer cylindrical housing 22 is formed at least partially of metal and is part of the electrical circuit connecting the control circuitry 11, the power supply 12, the puff sensor 16 and the heater 19.

Figure 3:
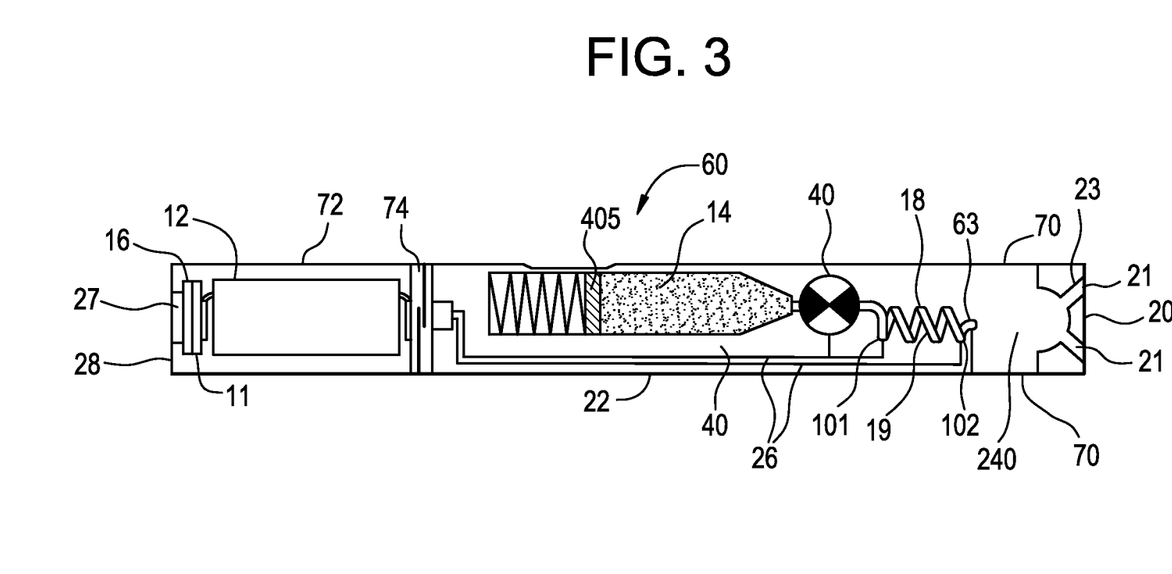
FIG. 3 is a longitudinal cross-sectional view of another example embodiment of an e-vaping device.

FIG. 3 is a cross-sectional view of an e-vaping device according to an example embodiment. As shown in FIG. 3, the e-vaping device 60 can also include a middle section (third section) 73, which can house the liquid pre-vaporization formulation reservoir 14 and the heater 19. The middle section 73 can be configured to be fitted with a threaded joint 74' at an upstream end of the first section or cartomizer 70 and a threaded joint 74 at a downstream end of the second section 72. In this example embodiment, the first section or cartomizer 70 houses the mouth-end insert 20, while the second section 72 houses the power supply 12 and the control circuitry 11 that is configured to control the power supply 12.

In at least one embodiment, the first section or cartomizer 70, the second section 72 and the third section 73 include a common outer cylindrical housing 22 extending in a longitudinal direction along the length of the e-vaping device 60. Moreover, in at least one embodiment, the middle section 73 is disposable and the first section or cartomizer 70 and/or second section 72 are reusable. The sections 70, 72, 73 can be attached by threaded connections or connectors 74 and 74' whereby the middle section 73 can be replaced when the reservoir 14 is used up. In another embodiment, the first section or cartomizer 70 is replaceable so as to avoid the need for cleaning the capillary tube 18 and/or heater 19. In at least one embodiment, the first section or cartomizer 70, the second section 72 and the middle section 73 may be integrally formed without threaded connections to form a disposable e-vaping device.

In the example embodiment illustrated in FIG. 3, the reservoir 14 is a tubular, elongated body formed of or including an elastomeric material so as to be flexible and/or compressible when squeezed. In at least one embodiment, the elastomeric material can be one of silicone, plastic, rubber, latex, and combinations thereof.

In at least one embodiment, the reservoir 14 is in fluid communication with a capillary tube 18 so that when squeezed, the reservoir 14 can deliver a volume of a pre-vaporization formulation such as a liquid material to the capillary tube 18. Contemporaneously to delivering pre-vaporization formulation to the capillary, the power supply 12 is activated upon the application of the manual pressure on the reservoir 14, and the capillary tube 18 is heated to form a heated section wherein the pre-vaporization formulation is volatilized. Upon discharge from the heated capillary tube 18, the volatilized material expands, mixes with air and forms a vapor.

As shown in FIG. 3, the reservoir 14 includes a valve 40 configured to maintain the liquid pre-vaporization formulation within the reservoir 14 and to open when the reservoir 14 is squeezed and pressure is applied to the reservoir 14. In at least one embodiment, the valve 40 opens when a critical, minimum pressure is reached so as to avoid inadvertent dispensing pre-vaporization formulation from the reservoir 14 or activating the heater 19. In at least one embodiment, the pressure required to press the pressure switch 44 is high enough such that accidental heating is avoided. Such arrangement avoids activation of the heater 19 in the absence of pre-vaporization formulation being pumped through the capillary. Once pressure upon the reservoir 14 is relieved, the valve 40 closes and the heated capillary tube 18 discharges any pre-vaporization formulation remaining downstream of the valve 40.

In an example embodiment, the pre-vaporization formulation includes a mixture of molecular nicotine (unprotonated and uncharged) and an acid, which protonates nearly all of the molecular nicotine in the pre-vaporization formulation, so that upon heating of the pre-vaporization formulation by a heater in the e-vaping device, a vapor having a majority amount of protonated nicotine and a minority amount of unprotonated nicotine is produced, whereby only a minor portion of all the volatilized (vaporized) nicotine typically remains in the gas phase of the vapor. The fraction of nicotine in the gas phase may contribute to perceptions of throat harshness and/or other perceived off-tastes. Reducing the proportional level of nicotine in the gas phase may improve the perceived subjective deficits associated with nicotine in the gas phase. For example, although the pre-vaporization formulation may include up to 5% of nicotine, the proportion of nicotine in the gas phase of the vapor may be substantially 1% or less of the total nicotine in the pre-vaporization formulation.

In some embodiments, the amount of acid to be added to the pre-vaporization formulation may depend on the strength and volatility of the acid and the amount needed to adjust the pH of the pre-vaporization formulation to the desired range. If too much acid is added, most or substantially all of the available nicotine may be protonated and enter the particulate phase of the vapor, leaving very little unprotonated nicotine in the gas phase of the vapor and thus generating a vapor with not enough harshness to satisfy the taste expectations of the adult vaper. In contrast, if too little acid or an ineffective (weak) acid is added, a larger amount of nicotine may remain unprotonated and in the gas phase of the vapor so that the adult vaper may experience increased and possibly undesirable throat harshness. With pre-vaporization formulations having a nicotine content above approximately 2% by weight, and in the absence of the combinations of acids described herein, perceived throat harshness may approach levels which render the vapor unpleasant when inhaled by the adult vaper. With pre-vaporization formulations of nicotine content above approximately 4% by weight, and in the absence of the combination of acids as described herein, perceived throat harshness may approach levels rendering the vapor uninhalable by the adult vaper. With the addition of acids according to the teachings herein, perceived throat harshness is maintained at desirable levels, akin to the perceived throat harshness experienced with tobacco-based products.

According to at least one example embodiment, the acid has the ability to transfer into the vapor. Transfer efficiency of an acid is the ratio of the mass fraction of the acid in the vapor to the mass fraction of the acid in the liquid pre-vaporization formulation. In at least one embodiment, the acid or combination of acids has a liquid to vapor transfer efficiency of about 50% or greater, and for example about 60% or greater. For example, pyruvic acid, tartaric acid and acetic acid have vapor transfer efficiencies of about 50% or greater. In at least one embodiment, the pre-vaporization formulation includes an acid or a combination of acids having a vapor transfer efficiency of about 50% or greater.

Figure 4:
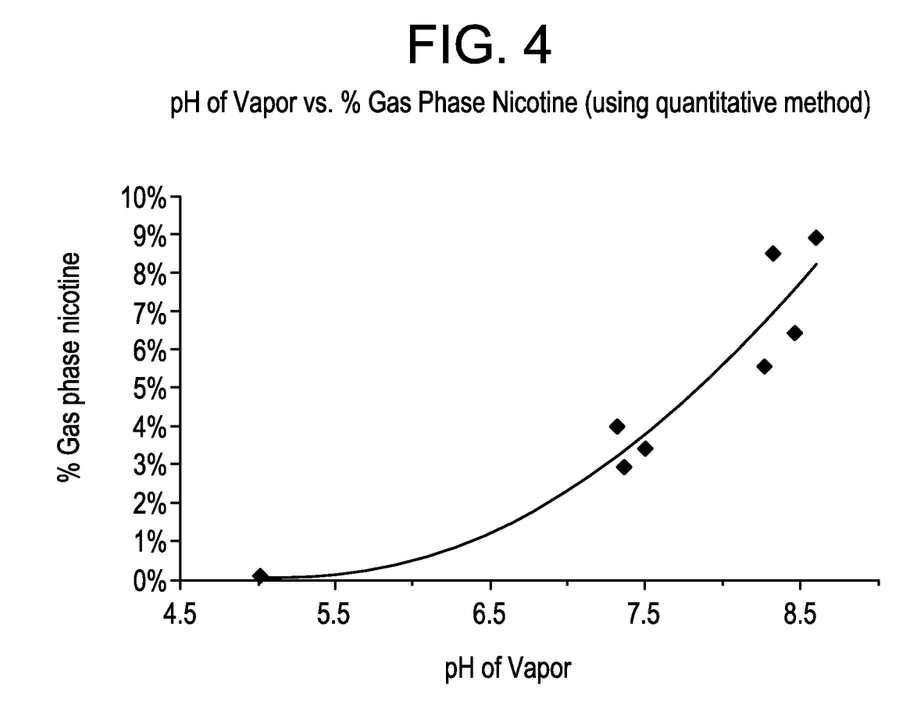
FIG. 4 illustrates the relationship between the concentration of nicotine in the gas phase and the pH of the pre-vaporization formulation.

According to at least one example embodiment, the acids have a boiling point of at least about 100° C., and may be included in the pre-vaporization formulation in an amount sufficient to adjust the pH of the pre-vaporization formulation in the range of about 3 to about 8. FIG. 4 illustrates the relationship between the concentration of nicotine in the gas phase and the pH of the vapor. In FIG. 4, the concentration of nicotine in the gas phase increases substantially when the pH is greater than about 6. Accordingly, a vapor having a pH that is lower than about 6 such as, for example, between about 4 to about 6, or between about 4.5 or 5.5, or a pH of about 5, may be advantageous in decreasing the concentration of nicotine in the gas phase, and thus may result in a vapor with less perceived harshness.

In at least one embodiment, the acid is included in the pre-vaporization formulation in an amount sufficient to reduce the amount of nicotine gas phase component by about 30% by weight or greater, about 60% to about 70% by weight, about 70% by weight or greater, of about 85% by weight or greater, of the level of nicotine gas phase component produced by a pre-vaporization formulation that does not include an acid.

According to at least one example embodiment, the pre-vaporization formulation includes one or more of pyruvic acid, formic acid, oxalic acid, glycolic acid, acetic acid, isovaleric acid, valeric acid, propionic acid, octanoic acid, lactic acid, levulinic acid, sorbic acid, malic acid, tartaric acid, succinic acid, citric acid, benzoic acid, oleic acid, aconitic acid, butyric acid, cinnamic acid, decanoic acid, 3,7-dimethyl-6-octenoic acid, 1-glutamic acid, heptanoic acid, hexanoic acid, 3-hexenoic acid, trans-2-hexenoic acid, isobutyric acid, lauric acid, 2-methylbutyric acid, 2-methylvaleric acid, myristic acid, nonanoic acid, palmitic acid, 4-pentenoic acid, phenylacetic acid, 3-phenylpropionic acid, hydrochloric acid, phosphoric acid, sulfuric acid, and combinations thereof. The acid also may be incorporated in the form of a salt. The pre-vaporization formulation also includes a vapor former, optionally water, and optionally flavorants.

As used herein, the term "vapor former" describes any suitable known compound or mixture of compounds that, in use, facilitates formation of a vapor and that is substantially resistant to thermal degradation at the operating temperature of the vapor-generating article. Suitable vapor-formers include, but are not limited to, polyhydric alcohols, such as propylene glycol, triethylene glycol, 1,3-butanediol and glycerin; esters of polyhydric alcohols, such as glycerol mono-, di- or triacetate; and aliphatic esters of mono-, di- or polycarboxylic acids, such as dimethyl dodecanedioate and dimethyl tetradecanedioate. Example vapor formers are polyhydric alcohols or mixtures thereof, such as propylene glycol, triethylene glycol, 1,3-butanediol and glycerin. The vapor-forming substrate may comprise a single vapor former such as, for example, glycerin. Alternatively, the vapor-forming substrate may comprise a combination of two or more vapor formers.

In at least one embodiment, the vapor former is one of propylene glycol, glycerin and combinations thereof. In another embodiment, the vapor former is glycerin. In at least one embodiment, the vapor former is included in an amount ranging from about 40% by weight based on the weight of the pre-vaporization formulation to about 90% by weight based on the weight of the pre-vaporization formulation (e.g., about 50% to about 80%, about 55% to about 75% or about 60% to about 70%). Moreover, in at least one embodiment, the pre-vaporization formulation can include propylene glycol and glycerin included in a ratio of about 3:2. In at least one embodiment, the ratio of propylene glycol and glycerin may be substantially 2:3 and 3:7.

The pre-vaporization formulation optionally includes water. Water can be included in an amount ranging from about 5% by weight based on the weight of the pre-vaporization formulation to about 40% by weight based on the weight of the pre-vaporization formulation, or in an amount ranging from about 10% by weight based on the weight of the pre-vaporization formulation to about 15% by weight based on the weight of the pre-vaporization formulation.

In at least one embodiment, the acid or combination of acids may be incorporated into the pre-vaporization formulation in the form of a salt. In at least one embodiment, the salt form of the acid is selected such that the addition of the acid does not have significant adverse effects on vapor transfer efficiency and/or the reaction of the corresponding free acid form with nicotine.

The acids included in the pre-vaporization formulation can have a boiling point of at least about 100° C. For example, the acids can have a boiling point ranging from about 100° C. to about 300° C., or about 150° C. to about 250° C. (e.g., about 160° C. to about 240° C., about 170° C. to about 230° C., about 180° C. to about 220° C. or about 190° C. to about 210° C.). By including acids having a boiling point within the above ranges, the acids may volatilize when heated by the heater element of the e-vaping device, as described above with respect to FIGS. 2 and 3. In at least one embodiment utilizing a heater coil and a wick, the heater coil may reach an operating temperature at or about 300° C.

The total acid content of the pre-vaporization formulation may range from about 0.1% by weight to about 6% by weight, or from about 0.1% by weight to about 2% by weight, based on the weight of the pre-vaporization formulation. The pre-vaporization formulation may also contain between up to 3% and 5% nicotine by weight. In at least one embodiment, the total acid content of the pre-vaporization formulation is less than about 3% by weight. In another embodiment, the total acid content of the pre-vaporization formulation is less than about 0.5% by weight. The pre-vaporization formulation may also contain between about 4.5% and 5% nicotine by weight. When tartaric acid, pyruvic acid, and/or acetic acid is used, the total acid content of the pre-vaporization formulation may be about 0.05% by weight to about 2% by weight, or about 0.1% by weight to about 1% by weight.

In at least one embodiment, pyruvic acid is included in an amount ranging from about 0.1% by weight to about 5.0% by weight, and for example about 0.5% by weight. Tartaric acid may be included in the pre-vaporization formulation in an amount ranging from about 0.1% by weight to about 5.0% by weight, and for example about 0.4% by weight. Acetic acid may be included in an amount ranging from about 0.1% by weight to about 5.0% by weight. In at least one embodiment, the entire acid content of the pre-vaporization formulation is less than about 3% by weight.

Furthermore, the acids may be selected and the concentrations thereof may be adjusted to maintain the desired low levels of gas phase nicotine, even at the more elevated nicotine content levels in the pre-vaporization formulation.

In example embodiments, the total acid content of the pre-vaporization formulation may range from about 0.1% by weight to about 6% by weight, such as from about 0.5% to about 4% by weight, or from about 1% to about 3% by weight, or from about 1.5% to about 2.5% by weight, or from about 0.1% by weight to about 2% by weight. For example, in embodiments, the total acid content of the pre-vaporization formulation may be from about 0.5% to about 2.5%, such as from about 1.5% to about 2.0% by weight based on the total weight of the pre-vaporization formulation, where the pre-vaporization formulation may contain from about 2 to about 5% nicotine, such as from about 2.5% to about 4.5% nicotine.

In embodiments, pyruvic acid is included in an amount ranging from about 0.1 to about 2% by weight based on the weight of the pre-vaporization formulation; tartaric acid is included in an amount ranging from about 0.1 to about 2% by weight based on the weight of the pre-vaporization formulation; and acetic acid is included in an amount ranging from about 0.1 to about 2% by weight based on the weight of the pre-vaporization formulation. In embodiments, a combination of pyruvic acid, tartaric and acetic acid is present in the pre-vaporization formulation in a total amount from about 0.1 to about 2% by weight based on the weight of the pre-vaporization formulation, such as from about 1.5 to about 2% by weight. In embodiments, pyruvic acid, tartaric and acetic acid are each added, for example in approximately equal amounts (equal by weight percent of the pre-vaporization formulation). The formulation may contain nicotine in an amount ranging from about 2% by weight to about 10% by weight, such as from about 2% to about 9%, or from about 2% to about 8%, or from about 2% to about 6%, or from about 2% to about 5%. For example, in embodiments, the formulation may contain nicotine in an amount from about 2.5% to about 4.5% based on the total weight of the pre-vaporization formulation. The formulation may also include nicotine bitartrate in concentrations ranging from about 0.5% to about 1.5%.

The pre-vaporization formulation may also include a flavorant in an amount ranging from about 0.01% to about 15% by weight (e.g., about 1% to about 12%, about 2% to about 10%, or about 5% to about 8%). The flavorant can be a natural flavorant or an artificial flavorant. In at least one embodiment, the flavorant is one of tobacco flavor, menthol, wintergreen, peppermint, herb flavors, fruit flavors, nut flavors, liquor flavors, and combinations thereof.

In embodiments, the nicotine is included in the pre-vaporization formulation in an amount ranging from about 2% by weight to about 6% by weight (e.g., about 2% to about 3%, about 2% to about 4%, about 2% to about 5%) based on the total weight of the pre-vaporization formulation. In at least one embodiment, the nicotine is added in an amount of up to about 5% by weight based on the total weight of the pre-vaporization formulation. In at least one embodiment, the nicotine content of the pre-vaporization formulation is about 2% by weight or greater based on the total weight of the pre-vaporization formulation. In another embodiment, the nicotine content of the pre-vaporization formulation is about 2.5% by weight or greater based on the total weight of the pre-vaporization formulation. In another embodiment, the nicotine content of the pre-vaporization formulation is about 3% by weight or greater based on the total weight of the pre-vaporization formulation. In another embodiment, the nicotine content of the pre-vaporization formulation is about 4% by weight or greater based on the total weight of the pre-vaporization formulation. In another embodiment, the nicotine content of the pre-vaporization formulation is about 4.5% by weight or greater based on the total weight of the pre-vaporization formulation.

By providing a pre-vaporization formulation comprising nicotine at concentrations of greater than 2% or more by weight, for example in the range of 2% to about 6% by weight, together with an addition of the acids to the pre-vaporization formulation in accordance with the example embodiments, the perceived sensory benefits for the adult vaper associated with the higher nicotine levels is achieved (warmth in the chest), while also avoiding the sensory deficits previously associated with higher nicotine levels (excessive harshness in the throat).

The following examples of e-vaping devices are discussed:

EXAMPLE 1

A pre-vaporization formulation including about 3% of nicotine by weight, 80% glycerine and 20% water. The pre-vaporization formulation also includes about 1% nicotine bitartrate salt, about 0.5% pyruvic acid and 0.25% acetic acid by weight. The generated vapor has a milder throat harshness during both inhaling and exhaling compared to a pre-vaporization formulation that does not include the above components in the above concentrations without lending an excessively acidic taste to the vapor.

EXAMPLE 2

A pre-vaporization formulation including about 3% of nicotine by weight, 80% glycerine and 20% water. The pre-vaporization formulation also includes a total concentration of about 2% of a combination of tartaric acid, pyruvic acid and acetic acid by weight in substantially equal concentrations.

EXAMPLE 3

A pre-vaporization formulation including about 3% of nicotine by weight, 80% glycerine and 20% water. The pre-vaporization formulation also includes about 0.5% of a combination of tartaric acid, about 1% pyruvic acid and about 0.5% acetic acid by weight.

EXAMPLE 4

A pre-vaporization formulation including about 3% of nicotine by weight, 80% of a combination of glycerine and propylene glycol, and 20% water. The pre-vaporization formulation also includes about 0.25% of a combination of tartaric acid, about 1% pyruvic acid and about 0.75% acetic acid by weight.

Example embodiments having thus been described, it will be obvious that the same may be varied in many ways. Such variations are not to be regarded as a departure from the intended spirit and scope of example embodiments, and all such modifications as would be obvious to one skilled in the art are intended to be included within the scope of the following claims.

The invention claimed is:

1. A pre-vaporization formulation of an e-vaping device, the pre-vaporization formulation comprising:
a vapor former;
nicotine;
nicotine bitartrate in a concentration of about 0.5% to about 2%; and
a combination of a plurality of acids;
wherein a pH of the pre-vaporization formulation is between about 4 and about 6, and wherein the combination of the plurality of acids includes formic acid, oxalic acid, glycolic acid, acetic acid, isovaleric acid, valeric acid, propionic acid, octanoic acid, lactic acid, sorbic acid, malic acid, tartaric acid, succinic acid, citric acid, benzoic acid, oleic acid, aconitic acid, butyric acid, cinnamic acid, decanoic acid, 3,7-dimethyl-6-octenoic acid, 1-glutamic acid, heptanoic acid, hexanoic acid, 3-hexenoic acid, trans-2-hexenoic acid, isobutyric acid, lauric acid, 2-methylbutyric acid, 2-methvlvaleric acid, myristic acid, nonanoic acid, palmitic acid, 4-pentenoic acid, phenylacetic acid, 3-phenvlpropionic acid, hydrochloric acid, phosphoric acid and sulfuric acid.

2. The pre-vaporization formulation of claim 1, wherein the pH of the pre-vaporization formulation is between about 4.5 and 5.5.

3. The pre-vaporization formulation of claim 1, wherein the pH of the pre-vaporization formulation is about 5.

4. The pre-vaporization formulation of claim 1, wherein a concentration of the combination of a plurality of acids is between about 0.25% and about 2%.

5. The pre-vaporization formulation of claim 1, wherein the combination of acids includes equal parts of each of the tartaric acid and the acetic acid.

6. The pre-vaporization formulation of claim 1, wherein a concentration of the nicotine is between about 1.5% by weight and about 6% by weight.

7. The pre-vaporization formulation of claim 1, wherein a concentration of the nicotine bitartrate is between about 0.5% by weight and about 1.5% by weight.

8. The pre-vaporization formulation of claim 1, wherein the concentration of nicotine bitartrate is about 0.5% to 1% and wherein a concentration of a mixture of about equal parts tartaric acid and acetic acid is about 0.5% to 1%.

9. The pre-vaporization formulation of claim 1, wherein the concentration of nicotine bitartrate is about 0.5% to 1% and wherein a concentration of hydrochloric acid is about 0.01% to 0.1%.

10. The pre-vaporization formulation of claim 1, wherein a concentration of oleic acid is about 0.5% to 1% and a concentration of a mixture of about equal parts tartaric acid and acetic acid is about 0.5% to 1.5%.

11. The pre-vaporization formulation of claim 1, wherein a concentration of sorbic acid is about 0.1% to 0.5%, a concentration of tartaric acid is about 0.1% to 0.5%.

12. The pre-vaporization formulation of claim 1, wherein a concentration of succinic acid is about 0.1% to 0.5%, and a concentration of lactic acid is about 0.1% to 0.5%.

13. The pre-vaporization formulation of claim 1, wherein the combination of acids includes about 15% to 35% of each of the tartaric acid and the acetic acid.

14. The pre-vaporization formulation of claim 1, wherein the combination of acids includes about 10% to 40% of each of the tartaric acid and the acetic acid.

15. The pre-vaporization formulation of claim 1, wherein the combination of acids includes about 5% to 45% of each of the tartaric acid and the acetic acid.

16. The pre-vaporization formulation of claim 1, wherein the combination of acids includes less than about 50% of each of the tartaric acid and the acetic acid.

17. An e-vaping device, comprising:
a cartomizer including a reservoir holding a pre-vaporization formulation, a mouth piece and a heater configured to heat the pre-vaporization formulation; and
a power supply section removably connected to the cartomizer via a connector and including a sensor housed in a housing, a sensor holder holding the sensor, and a power source disposed in the power supply section and configured to supply power to the heater;
wherein the pre-vaporization formulation includes:
a vapor former;
nicotine;
nicotine bitartrate in a concentration of about 0.5% to about 2%; and
a combination of acids;
wherein a pH of the pre-vaporization formulation is between about 4 and about 6, and
wherein the combination of acids includes formic acid, oxalic acid, glycolic acid, acetic acid, isovaleric acid, valeric acid, propionic acid, octanoic acid, lactic acid, sorbic acid, malic acid, tartaric acid, succinic acid, citric acid, benzoic acid, oleic acid, aconitic acid, butyric acid, cinnamic acid, decanoic acid, 3,7-dimethyl-6-octenoic acid, 1-glutamic acid, heptanoic acid, hexanoic acid, 3-hexenoic acid, trans-2-hexenoic acid, isobutyric acid, lauric acid, 2-methylbutyric acid, 2-methylvaleric acid, myristic acid, nonanoic acid, palmitic acid, 4-pentenoic acid, phenylacetic acid, 3-phenylpropionic acid, hydrochloric acid, phosphoric acid and sulfuric acid.

18. The pre-vaporization formulation of claim 17, wherein the concentration of nicotine bitartrate is about 0.5% to 1%, and a concentration of a mixture of tartaric acid and acetic acid is about 0.5% to 1%.

19. The pre-vaporization formulation of claim 17, wherein the concentration of nicotine bitartrate is about 0.5% to 1%, and a concentration of hydrochloric acid is about 0.01% to 0.1%.

20. The pre-vaporization formulation of claim 17, wherein a concentration of oleic acid is about 0.5% to 1%, and a concentration of a mixture of tartaric acid and acetic acid is about 0.5% to 1.5.

21. The pre-vaporization formulation of claim 17, wherein a concentration of sorbic acid is about 0.1% to 0.5% and a concentration of tartaric acid is about 0.1% to 0.5%.

22. The pre-vaporization formulation of claim 17, wherein a concentration of succinic acid is about 0.1% to 0.5% and a concentration of lactic acid is about 0.1% to 0.5%.

23. A pre-vaporization formulation of an e-vaping device, the pre-vaporization formulation comprising:
a vapor former including of propylene glycol, glycerin, or both propylene glycol and glycerin;
nicotine at a concentration of about 6%;
nicotine salt at a concentration of about 0.5% to about 1%; and
a combination of acids including formic acid, oxalic acid, glycolic acid, acetic acid, isovaleric acid, valeric acid, propionic acid, octanoic acid, lactic acid, sorbic acid, malic acid, tartaric acid, succinic acid, citric acid, benzoic acid, oleic acid, aconitic acid, butyric acid, cinnamic acid, decanoic acid, 3,7-dimethyl-6-octenoic acid, 1-glutamic acid, heptanoic acid, hexanoic acid, 3-hexenoic acid, trans-2-hexenoic acid, isobutyric acid, lauric acid, 2-methylbutyric acid, 2-methylvaleric acid, myristic acid, nonanoic acid, palmitic acid, 4-pentenoic acid, phenylacetic acid, 3-phenylpropionic acid, hydrochloric acid, phosphoric acid and sulfuric acid;
wherein a pH of the pre-vaporization formulation is about 6.

* * * * *